US008021161B2

(12) United States Patent
LaFrance et al.

(10) Patent No.: US 8,021,161 B2
(45) Date of Patent: Sep. 20, 2011

(54) SIMULATED HEART VALVE ROOT FOR TRAINING AND TESTING

(75) Inventors: Hugues LaFrance, Mission Viejo, CA (US); Robert Stobie, Laguna Woods, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1480 days.

(21) Appl. No.: 11/414,954

(22) Filed: May 1, 2006

(65) Prior Publication Data
US 2007/0254273 A1 Nov. 1, 2007

(51) Int. Cl.
G09B 23/28 (2006.01)
(52) U.S. Cl. .......... 434/267; 434/262; 434/272
(58) Field of Classification Search .......... 434/262–275; 623/1.24, 1.26, 1.1, 2.42
See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionexcu et al. |
| 4,106,129 A | 8/1978 | Carpentier et al. |
| 4,172,295 A | 10/1979 | Batten |
| 4,217,665 A | 8/1980 | Bex |
| 4,218,782 A | 8/1980 | Rygg |

(Continued)

FOREIGN PATENT DOCUMENTS
EP 0 084 395 8/1986
(Continued)

OTHER PUBLICATIONS

International Search Report for Patent Application No. PCT/US2007/067946.

(Continued)

*Primary Examiner* — Xuan Thai
*Assistant Examiner* — Timothy A Musselman
(74) *Attorney, Agent, or Firm* — AnneMarie Kaiser, Esq.

(57) ABSTRACT

A simulated heart valve root used for training physicians in techniques of implantation of prosthetic heart valves as well as for more realistically testing the efficacy of prosthetic heart valves. The simulated heart valve root is made of the flexible, tubular body having an inner wall defining an annular ledge within which the prosthetic heart valve is implanted. Discrete nodes or areas of simulated calcification may be provided on the annular ledge. A simulated aortic root includes alternating cusps and commissures with calcification simulated at least at one of the commissures. A tear in the annular ledge may also be provided which simulates a tear that might occur from a valvuloplasty procedure. A reinforcing sleeve may surround the flexible tubular body to provide rigidity or hoop strength thereto. A method of testing includes mounting the simulated heart valve root in a flow conduit, implanting a prosthetic heart valve in the root, applying pulsatile flow to the assembly, and monitoring for leaks. The simulated heart valve root may also be incorporated within a larger simulated heart for use in training physicians to remotely implant prosthetic heart valves.

2 Claims, 4 Drawing Sheets

U.S. PATENT DOCUMENTS

| | | | |
|---|---|---|---|
| 4,259,753 A | 4/1981 | Liotta et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,917,097 A | 4/1990 | Proudian et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,951,301 A * | 9/1999 | Younker ........................ 434/272 |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,062,866 A | 5/2000 | Prom |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,234,804 B1 | 5/2001 | Yong |
| 6,241,765 B1 | 6/2001 | Griffin et al. |
| 6,245,102 B1 | 6/2001 | Jayaraman |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,371,983 B1 | 4/2002 | Lane |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roeche et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,846,324 B2 | 1/2005 | Stobie |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,083,418 B2 * | 8/2006 | Baldauf ........................ 434/272 |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |

| | | |
|---|---|---|
| 7,556,647 B2 | 7/2009 | Drews et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0117009 A1 | 6/2004 | Cali et al. |
| 2004/0122514 A1 | 6/2004 | Fogarty et al. |
| 2004/0122516 A1 | 6/2004 | Fogarty et al. |
| 2004/0167573 A1 | 8/2004 | Williamson, IV et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0130107 A1 | 6/2005 | Ellingson et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004442 A1 | 1/2006 | Spenser et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0246888 A1 | 11/2006 | Bender et al. |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0319543 A1 | 12/2008 | Lane |
| 2009/0036903 A1 | 2/2009 | Ino et al. |
| 2009/0192599 A1 | 7/2009 | Lane et al. |

FOREIGN PATENT DOCUMENTS

| | | |
|---|---|---|
| EP | 0 096 721 | 12/1987 |
| EP | 0 125 393 | 12/1987 |
| EP | 0 179 562 | 7/1989 |
| EP | 0 143 246 | 11/1991 |
| EP | 1171059 | 1/2002 |
| GB | 2 056 023 | 3/1981 |
| GB | 2069843 | 9/1981 |
| GB | 2254254 | 10/1992 |
| GB | 2 279 134 | 12/1994 |
| GB | 2 338 582 A | 12/1999 |
| GB | 2338582 | 12/1999 |
| SU | 1116573 | 7/1985 |

| | | |
|---|---|---|
| WO | WO 89/00084 | 2/1989 |
| WO | WO 91/15167 | 10/1991 |
| WO | WO 92/01269 | 8/1992 |
| WO | WO 92/13502 | 8/1992 |
| WO | WO 92/19184 | 11/1992 |
| WO | WO 92/19185 | 11/1992 |
| WO | WO 97/09933 | 9/1995 |
| WO | WO 97/09944 | 9/1995 |
| WO | WO 95/28899 | 11/1995 |
| WO | WO 96/40006 | 12/1996 |
| WO | WO 97/27799 | 1/1997 |
| WO | WO 99/15112 | 9/1997 |
| WO | WO 97/41801 | 11/1997 |
| WO | WO 97/42871 | 11/1997 |
| WO | WO 98/06329 | 2/1998 |
| WO | WO 99/11201 | 3/1999 |
| WO | WO 99/51169 | 10/1999 |
| WO | WO 00/32105 | 6/2000 |
| WO | WO 00/60995 | 10/2000 |
| WO | WO 2006/086135 | 8/2006 |

OTHER PUBLICATIONS

International Search Report PCT/US2007/067946/ International Filing Jan. 5, 2007.
The Chamberlain Group, "Clear Aortic Root", Apr. 1, 2006, 1 page.
The Chamberlain Group, "Aortic Root", Apr. 1, 2006, 1 page.

* cited by examiner

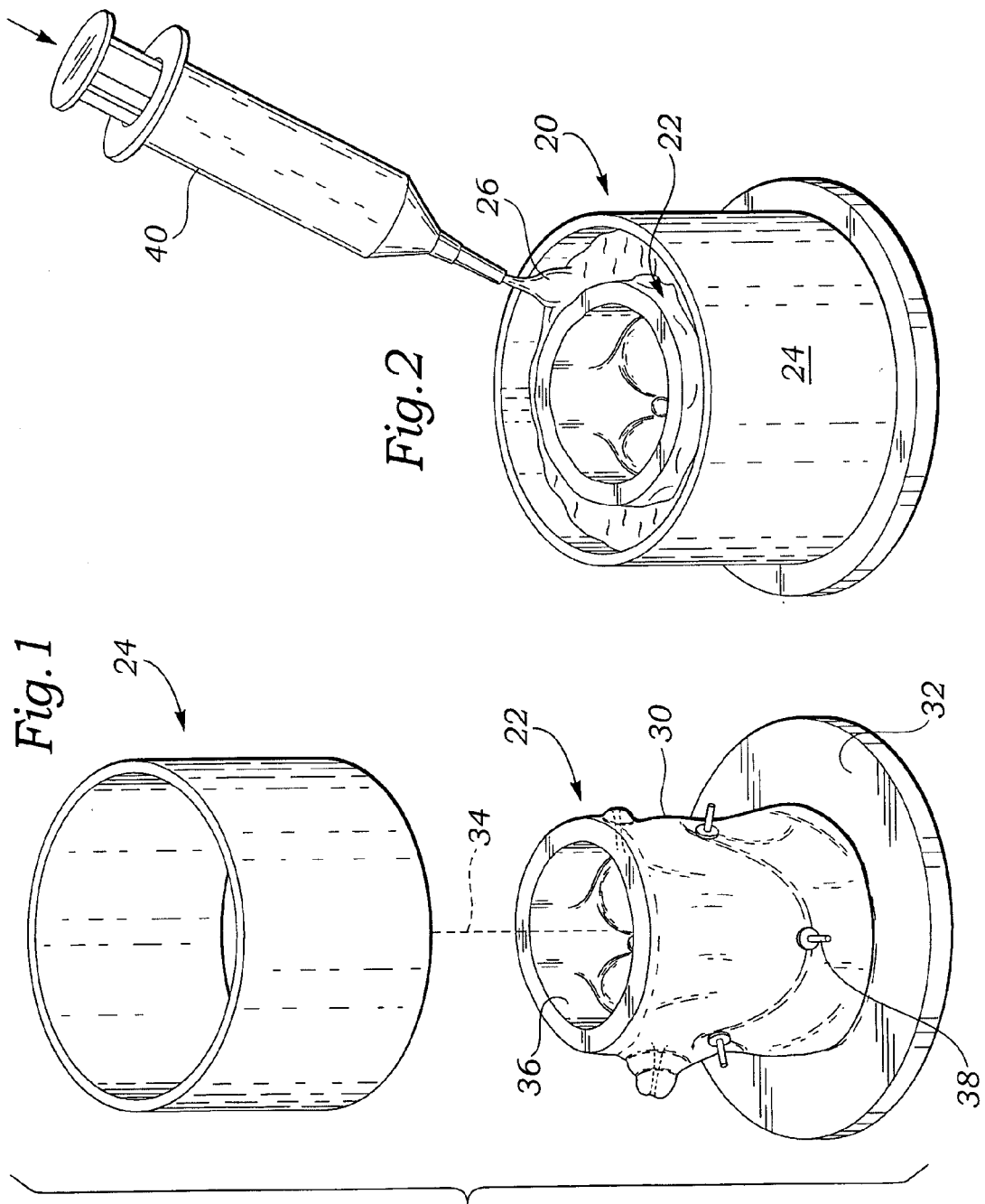

SIMULATED HEART VALVE ROOT FOR TRAINING AND TESTING

FIELD OF THE INVENTION

The present invention relates to fixtures and methods for testing the performance of prosthetic heart valves and, in particular, a simulated diseased heart valve root for a more realistic test.

BACKGROUND OF THE INVENTION

Heart valve replacement may be indicated when there is a narrowing of the native heart valve, commonly referred to as stenosis, or when the native valve leaks or regurgitates, such as when the leaflets are calcified. In one therapeutic solution, the native valve may be excised and replaced with either a biologic or a mechanical valve. Prosthetic valves attach to the patient's fibrous heart valve annulus, with or without the leaflets being present.

Conventional heart valve surgery is an open-heart procedure that is highly invasive, resulting in significant risks include bleeding, infection, stroke, heart attack, arrhythmia, renal failure, adverse reactions to the anesthesia medications, as well as sudden death. Fully 2-5% of patients die during surgery. The average hospital stay is between 1 to 2 weeks, with several more weeks to months required for complete recovery.

In recent years, advancements in "minimally-invasive" surgery and interventional cardiology have encouraged some investigators to pursue replacement of heart valves using remotely-implanted expandable valves without opening the chest or putting the patient on cardiopulmonary bypass. For instance, Percutaneous Valve Technologies ("PVT") of Fort Lee, N.J. and Edwards Lifesciences of Irvine, Calif., have developed a balloon-expandable stent integrated with a bioprosthetic valve. The stent/valve device is deployed across the native diseased valve to permanently hold the valve open, thereby alleviating a need to excise the native valve. PVT's device is designed for percutaneous delivery in a cardiac catheterization laboratory under local anesthesia using fluoroscopic guidance, thereby avoiding general anesthesia and open-heart surgery. Other percutaneously- or surgically-delivered expandable valves are also being tested. For the purpose of inclusivity, the entire field will be denoted herein as the delivery and implantation of expandable valves.

Expandable heart valves use either balloon-or self-expanding stents as anchors. In an aortic valve replacement procedure in particular, accurate placement of the prosthetic valve relative to the annulus and coronary ostia is important. Perhaps more critical, the uniformity of contact between the expandable valve and surrounding annulus, with or without leaflets, should be such that no paravalvular leakage occurs. This is sometimes difficult given the highly calcified condition of the aortic annulus in particular. Furthermore, due to the remote nature of expandable valve replacement procedures, the physician does not have the luxury of carefully positioning and then securing the periphery of the valve to the annulus with sutures, as with conventional open-heart techniques. Therefore, some have proposed various means for sealing the valve against the annulus, including providing sacs filled with sealing material around the exterior of the valve as in U.S. Patent Publication No. 2005-0137687 to Salahieh, et al. Other techniques for detecting leaks and/or sealing around expandable valves are disclosed in Spenser, et al., U.S. Patent Publication No. 2006-0004442.

Short of clinical trials, animal models (i.e., ovine and porcine) have been used in an attempt to evaluate the paravalvular and migration performance of both minimally invasive surgical (MIS) and percutaneous aortic valves. However, the animals used are typically healthy specimens whose heart valves are unlike the calcified or otherwise distorted annuluses of the typical prosthetic valve recipient. Implantation training is often done using animal models as well.

Due to the intense current interest in expandable prosthetic heart valves, there is a need for a better means for ensuring the efficacy of these valves and for training physicians in the new techniques of implantation.

SUMMARY OF THE INVENTION

The present invention provides a simulated heart valve root that more faithfully re-creates the anatomy of a diseased patient. The aortic root may be used for training purposes, or alternatively in a flow tester to examine the implanted valve in use for paravalvular leaks. The simulated heart valve root may be incorporated into a simulated heart for more realistic training purposes.

In one embodiment, the present invention provides a simulated human heart valve root, comprising a flexible, generally tubular body having an inner wall defining an annular ledge having a feature simulating an abnormal pathology incorporated therein.

For example, the feature simulating an abnormal pathology may be simulated calcification. Desirably, the simulated calcification is provided by at least one discrete node made of a material that is harder than the tubular body. The discrete node may be formed by the head of a pin passed through the tubular body. In an exemplary embodiment, the heart valve root is an aortic root such that the annular ledge has alternating cusps and commissures, and wherein the simulated calcification is provided by a plurality of discrete nodes distributed around the annular ledge, at least one of which is located at one of the commissures. Alternatively, the simulated calcification is provided by areas of hardness around the annular ledge. Desirably, the tubular body has a Shore A hardness of between about 5A and 40A and the simulated calcification is made of a material that is harder than the tubular body. The feature simulating an abnormal pathology may also comprise a tear in the annular ledge.

The present invention also provides a simulated human heart valve root system, comprising a flexible, generally tubular body having an inner wall defining an annular ledge, and a reinforcing sleeve surrounding the tubular body that has greater hoop strength than the tubular body. The reinforcing sleeve is desirably made of the material is harder than the material of the tubular body. In one embodiment, the reinforcing sleeve is molded around the tubular body so as to be in intimate contact with the entire exterior wall of the tubular body. For example, the reinforcing sleeve comprises an outer sleeve made of a rigid material and an intermediate sleeve formed of a hardenable material poured into an annular space between the outer sleeve and the tubular body.

Another aspect of the invention is a method of testing a prosthetic heart valve, including the steps of providing a simulated heart valve root, securing a prosthetic heart valve to be tested within the heart valve root, and applying pulsatile flow to the prosthetic heart valve within the heart valve root. The simulated heart valve root includes a tubular body formed of a flexible material and defining an annular ledge including a feature simulating an abnormal pathology incorporated into the annular ledge. Such a feature may comprise simulated calcification or a tear in the annular ledge. The method may further include monitoring for leaks around the periphery of the prosthetic heart valve within the heart valve root.

The present invention also provides a system for training a physician to implant a prosthetic heart valve, including a simulated heart defined by an entire simulated heart or portion thereof. A simulated heart valve root mounts in the simulated heart and is open to an access port for introducing a prosthetic heart valve. The simulated heart valve root includes a tubular body formed of a flexible material and defining an annular ledge. The annular ledge of the simulated heart valve root may further include a feature simulating an abnormal pathology, such a simulated calcification or a simulated tear in the annular ledge. Preferably, the feature simulating an abnormal pathology is radiopaque and the flexible material is not.

In a supplement to the training system, a means for vibrating the simulated heart is provided for more realism. Furthermore, a simulated radiopaque rib cage or spinal column may be provided around the simulated heart.

In a further aspect of the invention, a method of training a physician to implant a prosthetic heart valve utilizes a simulated heart valve root including a tubular body formed of a flexible material and defining an annular ledge. The heart valve root is mounted in a fixture having an access port, and physicians are instructed in delivering and implanting a prosthetic heart valve within the heart valve root. For more realism, the fixture may be subject to vibratory motion, or fluid may be directed through the heart valve root.

The method desirably includes blocking direct visual access to the heart valve root and providing a system for indirectly visualizing the step of delivering and implanting the prosthetic heart valve. The annular ledge of the simulated heart valve root may include a radiopaque feature simulating an abnormal pathology, wherein the system for indirectly visualizing can distinguish between radiopaque and non-radiopaque materials. In one embodiment, the fixture comprises a simulated heart including an entire simulated heart or portion thereof. Optionally, at least one additional radiopaque anatomical feature may be provided around the simulated heart, such as the rib cage or spinal column.

Another method of the present invention for training a physician to implant a prosthetic heart valve includes providing a simulated heart valve root including a tubular body formed of a flexible material and defining an annular ledge. The heart valve root mounts in a simulated heart including an entire simulated heart or portion thereof which blocks direct visual access to the heart valve root. Concurrently, a system for indirectly visualizing the heart valve root is provided. Desirably, the heart valve root includes a feature simulating an abnormal pathology, and the system for indirectly visualizing can distinguish between the feature in the flexible material.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIG. 1 is an exploded perspective view of two components of an exemplary simulated aortic root system of the present invention;

FIG. 2 is a perspective view of the exemplary simulated aortic root system of FIG. 1 during assembly;

DETAILED DESCRIPTION OF THE PREFERRED EMBODIMENTS

Figure 3:
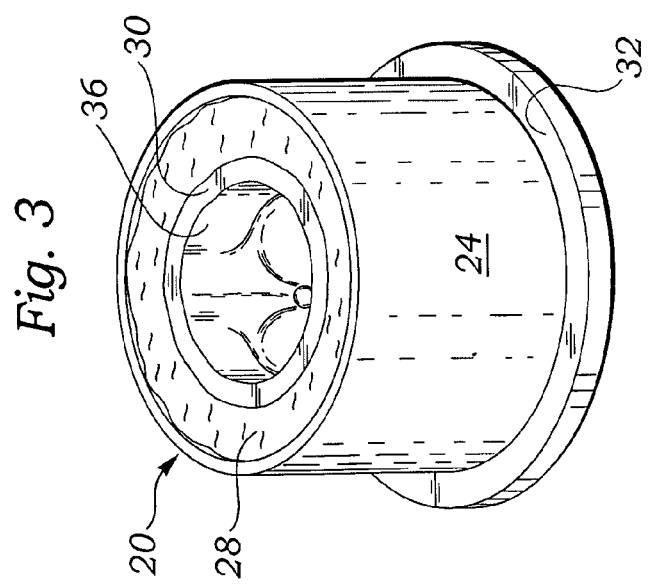
FIG. 3 is an assembled perspective view of the simulated aortic root system.

The present invention provides a simulated aortic root that is constructed to more realistically mimic the diseased annulus of the typical patient. No specifically, the simulated aortic root of the present invention provides calcification and other anatomical abnormalities that more faithfully re-creates the diseased aortic root. These simulated features are critical in teaching positioning and deploying both MIS and percutaneous aortic valves. Moreover, the more realistic aortic root provides an invaluable tool for in vitro testing to assess the paravalvular and migration performance of MIS and percutaneous prosthetic valves.

In the context of the present invention, the term "aortic root" refers to at least the tubular section of the aorta (the large artery leaving the heart) that is attached to the heart. The natural aortic root includes the annulus (tough, fibrous ring) and leaflets of the aortic valve, and the openings where the coronary arteries attach (coronary ostia). The simulated aortic root of the present invention includes a tubular body having an inner wall that defines the annulus. Although the leaflets are not included in the exemplary simulated aortic root, it is conceivable that they may also be simulated to test implantation of prosthetic valves over the leaflets. Furthermore, although the present invention illustrates and describes a simulated aortic root, many of the principles described herein may be useful for simulating other heart valve annuluses; namely, the mitral, pulmonic, or tricuspid annuluses. For example, a mitral annulus that is distended or calcified may also be simulated. Therefore, the term "simulated heart valve root" can be understood to refer to that section of any of the human heart valves equivalent to the aortic root just defined.

To remove ambiguity, it is important to quantify the relative terms "flexible," "soft," and "hard" in the context of the present invention.

The simulated heart valve roots of the present invention include flexible, tubular bodies. In this sense, flexible means having tactile properties similar to the native heart valve root. The physical characteristics of the tissue of the native heart valve root may differ in the population, but in general it can be said to be "soft," in that it easily yields to pressure, but has structural integrity (as opposed to clay, for example) so that it maintains its general anatomical shape. For example, an exemplary material for the tubular body is silicone rubber, such as a Silastomer™ from Hernon Manufacturing, Inc. of Sanford, Fla.

In general, "hard" or "hardness" refers to the property of a material that does not yield to pressure as easily as the material of the simulated heart valve root. There are varying degrees of hardness, of course, and the present invention is not to be construed as limited to a particular level. The simulated heart valve root includes "areas of hardness" incorporated into the annular ledge which is broadly construed to mean that there are areas that withstand pressure longer, or conversely, yield to pressure later, than the material of the flexible, tubular body. One methodology for measuring the hardness of various soft biological tissue, including calcification in arteries, was developed at Lawrence Livermore laboratory and involves the use of a modified Atomic Force Microscope (AFM). The researcher, Mehdi Balooch, determined that calcified deposits were many orders of magnitude stiffer than the surrounding healthy artery wall. However, most techniques are designed to detect calcification, not necessarily measure its hardness, and an accurate quantification of the widely varying hardness properties of calcification is quite difficult. Therefore, the exemplary magnitudes of hardness provided below for the simulated heart valve roots are to be considered guides only.

In the illustrated embodiment, the areas of hardness are provided by a series of discrete nodes of hardness, in particular using the heads of a number of pins passed through the flexible, tubular bodies. This construction is relatively straightforward, but it should be understood that other ways to provide areas of hardness are available. The areas of hardness are primarily intended to simulate calcification in the simulated heart valve root, especially around the annulus. Calcification is typically more diffuse than the discrete nodes illustrated, and another way to simulate it is to co-mold areas of hardness using a different material than that of the tubular body. Another possible construction is to separately mold the annular ledge of a harder material than the flexible, tubular body and fasten it using adhesive or other such means to the inner wall of the body. Therefore, the term "areas of hardness" refers to discrete nodes or more continuous regions of harder material than the tubular body, however formed.

FIGS. 1-3 illustrates steps in the formation and a finished simulated aortic root system 20 of the present invention. With reference first to FIG. 1, two components of the system 20 include a simulated aortic root 22 and an outer sleeve 24. In the assembled system 20, a filler material 26 (shown during assembly in FIG. 2) creates an intermediate sleeve 28 (shown after assembly in FIG. 3) between the exterior wall of the aortic root 22 and the interior wall of the outer sleeve 24. The exemplary system 20 therefore basically consists of the concentrically arranged aortic root 22, intermediate sleeve 28, and outer sleeve 24. The functional interaction between these three main elements is described in more detail below, and it should be emphasized that there are other ways to obtain the desired properties.

The aortic root 22 is desirably molded from a material that is, when cured or hardened, flexible and soft to simulate native aortic wall tissue. The aortic root 22 comprises a generally tubular body 30 and a flat, circular base flange 32 extending outward from a lower end thereof. The tubular body 30 is nominally oriented about an axis 34 and defines an inner wall 36. The inner wall 36 includes certain simulated anatomical features that will be described in more detail below with respect to FIGS. 5-8. In addition, the positioning and purpose of a plurality of pins 38 extending through the tubular body 30 will be described below.

To assemble the system 20, the tubular outer sleeve is positioned concentrically about the axis 34 and around the tubular body 30. An applicator 40 then fills the annular space between the outer sleeve 24 and tubular body 30 with a curable material 26, as depicted in FIG. 2. Of course, other ways of providing the intermediate sleeve 28 surrounding the tubular body 30 are known, such as co-molding the sleeve directly into the exterior of the tubular body itself. However formed, the intermediate sleeve 28 is made of a material that is harder than the material of the tubular body 30. In an exemplary embodiment, the intermediate sleeve 28 is made of a polyvinylsiloxane, commonly used as dental print polymer.

It is important to understand that the intermediate sleeve 28 and the outer sleeve 24 together combine to form a "reinforcing sleeve" around the tubular body 30. The outer sleeve 24 is made of a metal or polymer that has much greater hoop strength than the tubular body 30 of the aortic root 22. By virtue of the intermediate sleeve 28, the hoop strength provided by the outer sleeve 24 is coupled to the tubular body 30. Therefore, when radially outward forces are exerted on the inner wall 36 of the tubular body 30, the intermediate sleeve 28 supported by the outer sleeve 24 indirectly imparts the additional hoop strength to the tubular body. As mentioned above, there are other ways to provide these reinforcing properties to the relatively soft tubular body 30. For example, the outer sleeve 24 may directly surround and contact the tubular body 30, without using an intermediate sleeve 28. However, by virtue of its initial liquid state, the intermediate sleeve 28 closely conforms around the exterior wall of the tubular body 30 and therefore provides more uniform reinforcing support. Conversely, the outer sleeve 24 may be removed after formation of the intermediate sleeve 28, with the material properties of the intermediate sleeve supplying the desired hoop strength. The goal of any particular construction is to provide a reinforcing sleeve surrounding the tubular body that adds overall hoop strength thereto, and may also add localized rigidity to some or all regions around the tubular body. The benefits of this construction will be explained in more detail below with regard to methods of use of the system.

Figure 4:
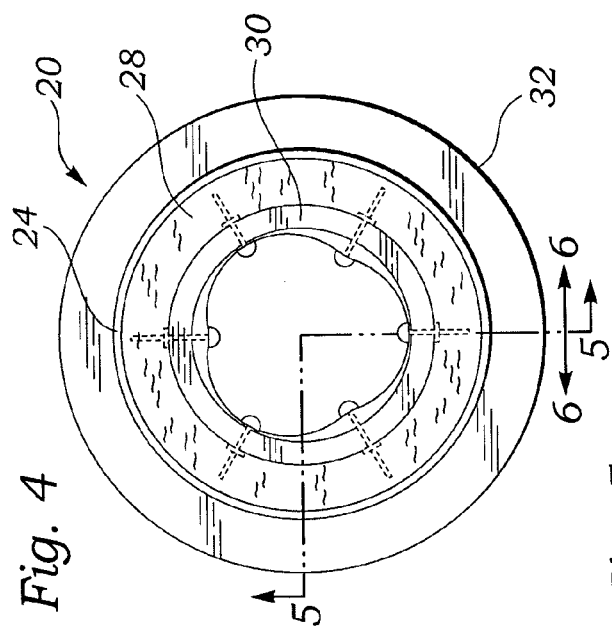
FIG. 4 is a top plan view of the exemplary simulated aortic root system.
Figure 5:
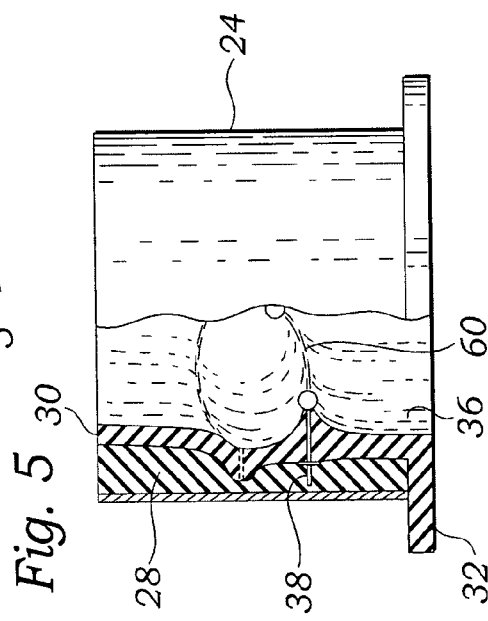
FIG. 5 is a partially sectioned elevational view of the simulated aortic root system.
Figure 6:
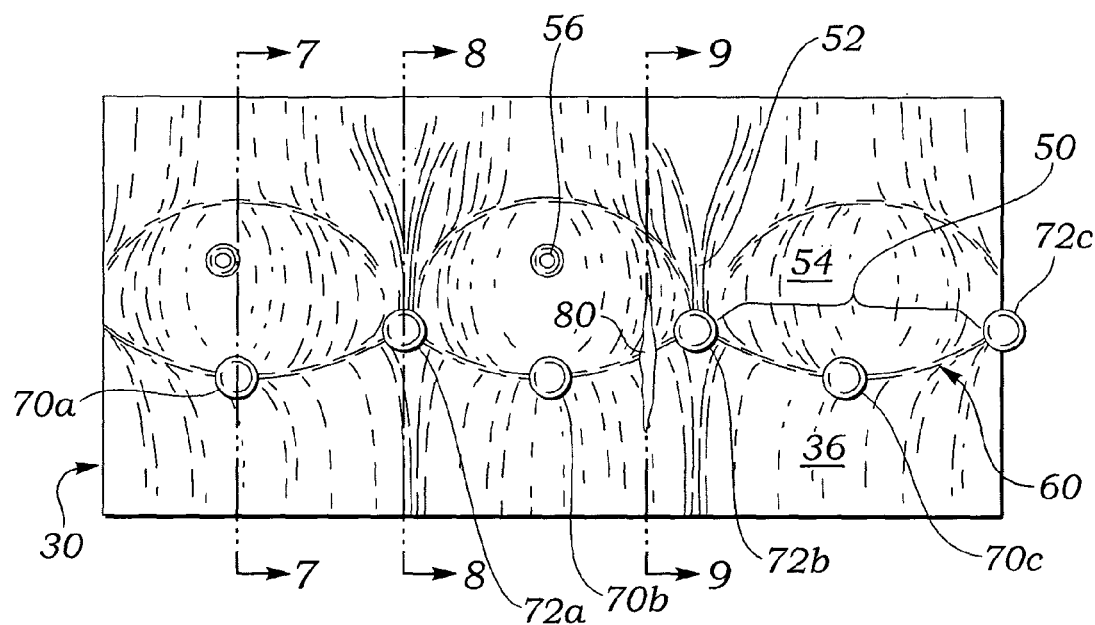
FIG. 6 is a layout view of a simulated aortic root used in the system of FIG. 1.

The exemplary construction of the simulated aortic root 22 will now be described with respect to FIGS. 4-8. FIG. 4 shows the aortic root system 20 from above, and illustrates the approximately equidistant circumferential placement of the pins 38. FIG. 6 shows the inner wall 36 of the tubular body 30 in plan view as if unrolled from the line 6-6 in FIG. 4. The exemplary contours of the inner wall 36 of a simulated aortic root are evident in FIG. 6. Specifically, the inner wall 36 simulates features of the aortic root including three arcuate cusps 50 separated by three upstanding commissures 52 (one of the commissures 52 is split and located at the far left and right edges). Rounded pockets or sinuses 54 bow outward above each of the cusps 50. Two openings or simulated coronary ostia 56 extend through the tubular body 30 at the approximate midpoint of two of the three sinuses 54.

Figure 7:
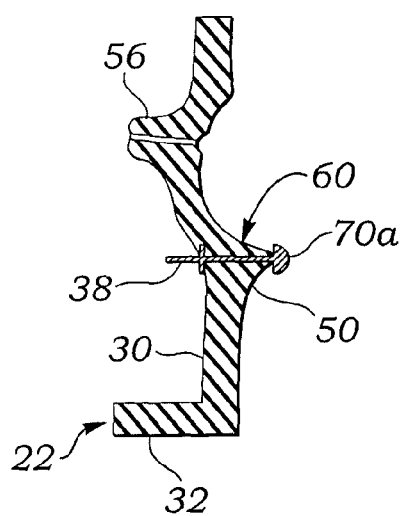
FIGS. 7-9 are radial sectional views through the simulated aortic root taken, respectively, along lines 7-7, 8-8, and 9-9 of FIG. 6.
Figure 8:
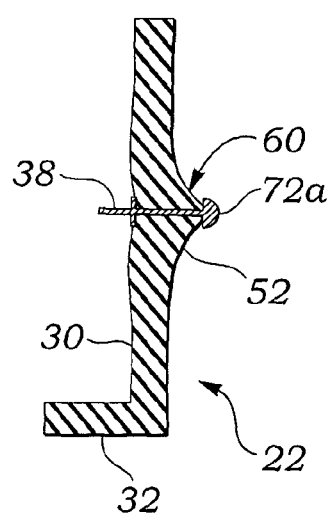

As seen best in FIGS. 6-8, an annular ledge 60 extends radially inward from the tubular body 30, following the undulating cusps 50 and commissures 52. In the plan view of FIG. 6, the annular ledge 60 defines somewhat of a wave shape with the cusps 50 defining the troughs and the commissures 50 the peaks. In the native aortic root, the annular ledge 60 comprises tougher, more fibrous tissue than the adjacent ascending aorta or ventricular tissue, and the native leaflets extend inward therefrom. In calcified heart valves, the regions of calcification are often concentrated about the leaflets and along the annular ledge 60.

As mentioned above, the present invention provides a simulated aortic root having areas, regions or nodes of calcification. The pins 38 pass through the tubular body 30 and terminate at their inner ends in pinheads simulating nodes of calcification. The pins 38 may be metallic or plastic, as long as the material is harder than the material of the tubular body 30. These discrete nodes may be positioned as desired in the tubular body 30, but are preferably placed along the annular ledge 60. In the illustrated embodiment, there are six pins 38 making six discrete nodes of calcification. Three nodes 70a, 70b, 70c are positioned at approximately the midpoint of each of the cusps 50, while three nodes 72a, 72b, 72c are positioned at each of the commissures 52. This distribution of the pins 38 is intended to be representative of the typical or average calcification along the annular ledge 60. Of course, as mentioned above, the discrete nature of the nodes as well as their specific construction are entirely exemplary, and other configurations are contemplated. One such configuration is to provide clusters of the pins 38 more unevenly spread along the annular ledge 60. Alternatively, a segment of elongated simulated calcification formed by a molded portion of the annular ledge 60 may be substituted for the discrete nodes. And finally, simulated calcified leaflets may also be added to the tubular body 30 to mimic the pathology prior to leaflet excision, which is sometimes the situation at the time of valve implantation.

In an exemplary configuration, the tubular body 30 is formed of a material that simulates the native arterial wall. For example, the tubular body 30 may be made of a silicone rubber having a hardness of about 5 Shore A durometer. However, to simulate overall calcification of the aortic root, the tubular body 30 may be formed of the silicone rubber having a hardness of 40A durometer. To further increase the stiffness, the tubular body 30 is constrained within the intermediate sleeve 28 which is made of a material that is even harder than the tubular body 30. Finally, the outer sleeve 24 provides an essentially rigid outer limit to deformation. In addition, the areas of hardness, such as the nodes 70a, 70b, 70c, are added to simulate uneven calcification within the aortic root. To summarize, the tubular body 30 desirably comprises a material having a hardness of between about 5A and 40A durometer supplemented by areas of hardness having a higher level of Shore A hardness.

Shore Hardness, using either the Shore A or Shore D scale, is the preferred method for rubbers/elastomers and is also commonly used for "softer" plastics such as polyolefins, fluoropolymers, and vinyls. The Shore A scale is used for "softer" rubbers while the Shore D scale is used for "harder" ones. The Shore A Hardness is the relative hardness of elastic materials such as rubber or soft plastics can be determined with an instrument called a Shore A durometer. If the indenter completely penetrates the sample, a reading of 0 is obtained, and if no penetration occurs, a reading of 100 results. The reading is dimensionless. Therefore, the areas of hardness have a Shore A value of greater than that of the material of the tubular body 30, up to 100. For example, if the tubular body 30 is made of a silicone rubber having a Shore A hardness of 40, the areas of hardness or nodes have a Shore A hardness of between 41-100. It should also be noted that the character of the areas of hardness or nodes need not be homogenous, and the magnitude of stiffness may vary within the areas of hardness.

Desirably, the areas of hardness or nodes are made of a radiopaque material. As will be explained below, the simulated heart valve root may be used to test the performance of expandable valves and to train physicians in their implantation. In doing so, the simulated calcification desirably shows up on X-ray or other imaging technique as it would in real life.

Figure 9:
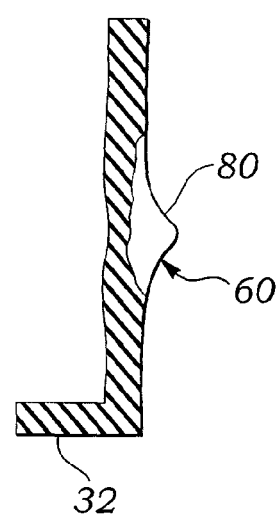

FIGS. 6 and 9 illustrates another feature of the simulated aortic root 22 that may be included to better mimic a diseased valve. Namely, a small groove or tear 80 is shown passing generally perpendicularly through the annular ledge 60. Such a vertical tear 80 may occur in natural diseased aortic valves after a valvuloplasty operation. That is, valvuloplasty involves expanding a balloon within the valve to increase the size of the orifice just prior to implant of a prosthetic valve. Sometimes, the annulus is calcified and somewhat brittle, and a valvuloplasty tends to break up the annular ledge at one or more points. Of course, this further increases the uneven nature of the implant site, and increases the chance for leakage around the implanted prosthetic valve. By simulating the tear 80, testing for leaks at the region near the tear may be performed after implantation of a prosthetic valve within the simulated aortic root 22.

Of course, the arbitrary nature of the exemplary nodes 70, 72 and tear 80 highlight the unpredictable nature of a diseased valve which can be simulated in the aortic root 22. For example, there may be more tears than areas of calcification, or vice versa, or there may be just a single region of calcification, or a pair diametrically opposed. It is even conceivable that an individual's annulus may be examined using endoscopy or other such imaging or scanning tools, and then in real-time a simulated aortic root may be created so that the physician can observe and practice on that model prior to the actual implantation procedure. Therefore, the present invention should most broadly be understood as providing at least one feature (calcification, tear, distention) simulating an abnormal pathology incorporated into the annular ledge.

In the past, animal models used to demonstrate the paravalvular and migration performance of both minimally invasive surgical (MIS) valves and percutaneous valves have been unable to simulate the simulate calcified or diseased aortic root. The intended patient population for such expandable valves typically have heavily calcified annuluses. The present invention simulates such a diseased annulus for relatively little cost. Prototypes of new expandable valves may be first tested within the simulated heart valve roots of the present invention to gauge efficacy; namely, anti-migration properties and paravalvular sealing.

The simulated heart valve roots of the present invention may become an integral part of validation of new prosthetic heart valves, in particular expandable valves. The realistic heart valve roots can be used both to verify the efficacy of the valves and to improve their design by identifying areas of leaking or migration. Fixtures for accelerated wear testing (AWT) of prosthetic heart valves have been used for many years. Most common is a pulsatile flow tester in which a prosthetic valve is secured within a tubular flow conduit through which fluid is pulsed back-and-forth to simulate the systolic-diastolic phases of the heart. Prosthetic valves may be subjected to long durations in the flow tester to test the valve integrity. It is even envisioned that the more realistic simulated heart valve roots of the present invention may become a required part of validation of new heart valves during the regulatory process. Currently, basic fatigue testing such as pulsatile accelerated wear testing is required, but the particular environment is not specified by the regulatory bodies. Due to the advent of new expandable valves, and the expected explosion of devices in this area, the present invention may provide a high level of confidence of the efficacy of the valves by providing a much more realistic testing regimen.

For simulated aortic roots, the present invention also permits the investigator to evaluate potential blockage of the coronary ostia 56 by different prosthetic heart valves. The physician may also examine the fit of the particular size of heart valve relative to the coronary ostia 56 to ensure that it will not occluded flow, which is a significant safety feature.

Another important aspect of the invention is the technique for constructing the particular shape of the flexible, tubular body 30. Ideally, a Computed Tomography (CT) scan of a human aortic root is performed, and a positive mold generated from the data. The positive mold defines the inner wall of the tubular body 30, which is then formed by applying the particular material such as silicone rubber around the positive mold. One useful option is to incorporate radio-opaque materials into the tubular body 30 as it is being formed to help visualize the implanted prosthetic heart valve during testing or training.

Another useful application for the realistic heart valve root is to incorporate it into a simulated heart unit as a teaching tool for physicians. The entire unit can be covered or otherwise placed outside of the physician's view, who is then tasked with remotely implanting a prosthetic valve into the heart valve root. Moreover, the heart valve root may be subject to oscillations or pulsatile flow to more faithfully re-create the beating heart movement and/or flow. The entire unit can be made portable so as to provide a highly cost effective and efficient way of familiarizing physicians with the implantation techniques.

Figure 10:
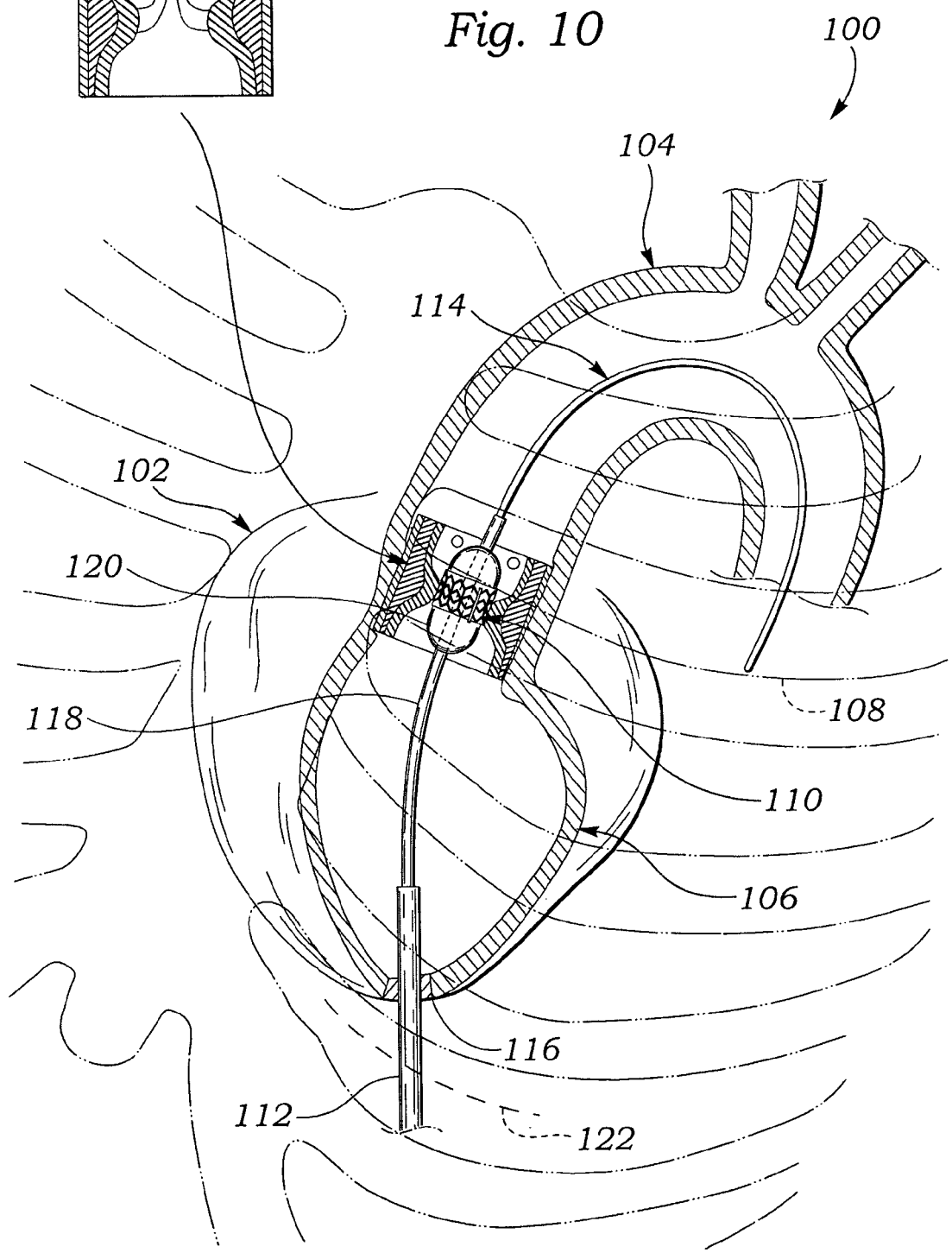
FIG. 10 is a sectional view of a simulated aortic root positioned within a training model of the heart, and showing a simulated chest cavity in phantom.

In an exemplary embodiment, FIG. 10 illustrates a simulated aortic root system 20 of the present invention incorporated into a larger portable training model 100. The training model 100 includes a simulated heart 102 having an aortic arch 104 connected to a left ventricle 106. The simulated heart 102 may include the entire heart, or may be limited to a portion thereof, such as a conduit/ventricle and valve annulus of interest. For example, the right atrium, mitral annulus, and left ventricle might be simulated instead. Furthermore, the training model 100 may include other anatomical features for a more realistic training regimen; for instance, a simulated rib cage 108 as seen in phantom or a simulated spinal column (not shown). As will be explained, these additional anatomical features are desirably made of a radiopaque material such that during training they show up on an X-ray, or another such system for indirectly visualizing the heart valve root that can distinguish between radiopaque and non-radiopaque material.

One possible used for the training model 100 is to teach surgeons or cardiologists how to implant expandable heart valves. In the illustrated embodiment, a delivery system is shown implanting an expandable valve 110 within the simulated aortic root system 20. There are numerous configurations of expandable valves, and the training model 100 may be used to test any of them. The delivery system includes a catheter or cannula 112 shown passing over a guide wire 114 through the apex 116 of the left ventricle 106 into the ventricular cavity, in a so-called antegrade transapical approach. A catheter 118 having a balloon 120 mounted thereon carries the expandable valve 110 to enable its expansion within the aortic root. Alternatively, a self-expanding valve may be implanted. Another approach is to pass the guide wire through the aortic arch 104 and downward toward the left ventricle 106. Such a retrograde approach is typically used with a percutaneous introduction of the balloon catheter 118.

Whichever method is used, an access port in the training model 100 opens to the particular annulus in which the prosthetic heart valve can be implanted. In the illustrated embodiment, an access port is formed at the apex 116 of the left ventricle 106, while for a percutaneous approach the access port could simply be an open end of the aortic arch, or a more realistic passage through simulated skin. For example, in the illustrated transapical approach, the access port may include an incision 122 formed through simulated tissue and located between two ribs, such as within the fifth intercostal margin as shown. It is even conceivable that the training model 100 may be incorporated within an entire simulated human body, but the very least it is covered or otherwise hidden from the physician's direct view.

The physician performs the valve implantation training under as realistic conditions as possible, including viewing the entire operation via a monitor or display headset that receives an X-ray image of the process. In this way, the surrounding structure such as the ribs 108 and spine (not shown) mimic the actual operation. For further verisimilitude, the simulated heart 102 may be mounted within a fixture that oscillates, vibrates, or rocks, and generally simulates the dynamic motion of the heart. To even further increase the realism of the entire training unit, a model that incorporates pulsatile fluid flow may be used. In such a version, the fluid systolic and diastolic forces are added such that the physician will be able to experience as near as possible the tactile sensation of implanting the valve numerous times on a simulated beating heart. Such experience is invaluable for a new technology, one for which each surgeon will likely demand a high level of comfort before replacing the known open-heart techniques.

In one example of incorporating pulsatile flow, systems that currently perform advanced wear testing (AWT) on heart valves or grafts could be incorporated into the training model 100. Desirably, a cardiac valve analyzer (e.g., Wieting) having acrylic chambers designed from RTV silicone rubber castings of human heart passages and associated blood vessels may be utilized to provide appropriate geometries for the valve delivery and hydrodynamic considerations. Saline impelled by an appropriate pump is then pulsed over the valve annulus site. Various flow meters, pressure transducer, optical sensors, and such may be incorporated for testing the valve or implant success, and one or more video scopes may be strategically placed to provide "instant replay" of the implant for debriefing purpose. Those of skill in the art will understand that many variations on this system are possible and individual valve manufacturers or teaching hospitals may wish to customize their own.

The advantages of the above-described training model 100 cannot be overestimated when considered in the context of the rapidly burgeoning field of expandable valves. Because of the drawbacks associated with conventional open-heart surgery, percutaneous and minimally-invasive surgical approaches are garnering intense attention. Although the technology is in its infancy, the implantation of expandable heart valves may become commonplace within the next 20 years. Perhaps the biggest hurdle to its acceptance is resistance from doctors who are understandably anxious about converting from an effective, if imperfect, regimen to a novel approach that promises great outcomes but is relatively foreign. By providing a realistic training model 100, expandable valves can be first tested again and again by manufactures in real conditions, and then the valves that prove efficacious may be implanted by surgeons so as to familiarize themselves with the particular product or approach. The inventors contemplate that in very short order of this training model 100 will become a "must have" tool in the training of physicians.

While the invention has been described in its preferred embodiments, it is to be understood that the words which have been used are words of description and not of limitation. Therefore, changes may be made within the appended claims without departing from the true scope of the invention.

What is claimed is:

1. A simulated human heart valve root configured to realistically mimic a diseased annulus for use in simulated heart valve replacement surgery, comprising:
   a flexible, generally tubular body having an inner wall defining an annular ledge; and
   a feature simulating an abnormal pathology incorporated into the annular ledge, wherein the feature simulating an abnormal pathology comprises simulated calcification, and
   wherein the heart valve root is an aortic root such that the annular ledge has alternating cusps and commissures, and wherein the simulated calcification is provided by a plurality of discrete nodes distributed around the annular ledge, at least one of which is located at one of the commissures, and the nodes are made of a material that is harder than the tubular body.

2. The simulated human heart valve root of claim 1, wherein the tubular body has a Shore A hardness of between about 5A and 40A.

* * * * *